(12) United States Patent
Wu et al.

(10) Patent No.: US 11,092,302 B2
(45) Date of Patent: Aug. 17, 2021

(54) ELECTRONIC ARTIFICIAL CANDLE

(71) Applicant: GUANGDONG LIGHTING SILK ROADS CULTURAL DEVELOPMENT CO., LTD, Guangdong (CN)

(72) Inventors: Wenfeng Wu, Guangdong (CN); Haicheng Cai, Guangdong (CN); Wei Wang, Guangdong (CN)

(73) Assignee: GUANGDONG LIGHTING SILK ROADS CULTURAL DEVELOPMENT CO., LTD, Guangzhou (CN)

(*) Notice: Subject to any disclaimer, the term of this patent is extended or adjusted under 35 U.S.C. 154(b) by 337 days.

(21) Appl. No.: 16/280,004

(22) Filed: Feb. 19, 2019

(65) Prior Publication Data
US 2019/0195447 A1    Jun. 27, 2019

Related U.S. Application Data

(63) Continuation of application No. PCT/CN2017/117593, filed on Dec. 21, 2017.

(51) Int. Cl.
| | |
|---|---|
| *F21S 10/04* | (2006.01) |
| *F21S 6/00* | (2006.01) |
| *B05B 1/14* | (2006.01) |
| *A61L 9/14* | (2006.01) |
| *A61M 21/02* | (2006.01) |
| *A61L 9/013* | (2006.01) |

(Continued)

(52) U.S. Cl.
CPC ............. *F21S 10/046* (2013.01); *A61L 9/013* (2013.01); *A61L 9/122* (2013.01); *A61L 9/14* (2013.01); *A61M 21/02* (2013.01); *B05B 1/14* (2013.01); *F21S 6/001* (2013.01); *A61L 2209/12* (2013.01); *A61L 2209/13* (2013.01); *A61M 2021/0016* (2013.01); *A61M 2205/587* (2013.01); *F21Y 2115/10* (2016.08)

(58) Field of Classification Search
CPC ... A61L 9/22; F21S 6/001; F21S 10/00; F21S 10/04; F21S 10/046; F21V 23/00
See application file for complete search history.

(56) References Cited

U.S. PATENT DOCUMENTS

| | | | | |
|---|---|---|---|---|
| 9,366,402 | B2* | 6/2016 | Li | F21S 6/001 |
| 9,664,349 | B1* | 5/2017 | Hurduc | H05B 45/20 |

(Continued)

FOREIGN PATENT DOCUMENTS

CN          202747231 U       2/2013

*Primary Examiner* — Daniel I Walsh

(57) ABSTRACT

An electronic artificial candle includes a barrel with a first through hole at a top. A mounting tube is fixed to an inner surface of the top of the barrel and has a top to which an elongate first bracket is snap-fitted. The first bracket is arranged radially. A second bracket is swingable suspended on the first bracket. An upper portion of the second bracket passes through the first through hole. The second bracket is arranged inside the barrel. A hollow and transparent flame cover is fixed to the top of the second bracket, inside which at least one LED is fixed. At least one magnet is fixed to a lower end of the second bracket. A magnetic coil is fixed to the bottom of the mounting tube. The LED and the magnetic coil are electrically connected to a power control board.

14 Claims, 5 Drawing Sheets

(51) Int. Cl.
*A61L 9/12* (2006.01)
*F21Y 115/10* (2016.01)
*A61M 21/00* (2006.01)

(56) References Cited

U.S. PATENT DOCUMENTS

| | | | | |
|---|---|---|---|---|
| 10,030,831 B2* | 7/2018 | Baeza | | F21S 9/03 |
| 10,054,276 B1* | 8/2018 | Li | | F21S 6/001 |
| 10,240,735 B1* | 3/2019 | Huang | | F21S 6/001 |
| 10,352,517 B2* | 7/2019 | Carpintero | | F21V 11/18 |
| 10,443,798 B1* | 10/2019 | Tan | | F21S 10/046 |
| 10,488,005 B2* | 11/2019 | Roberts | | G02B 6/0006 |
| 10,520,150 B2* | 12/2019 | Huang | | F21S 6/001 |
| 10,578,263 B2* | 3/2020 | Dong | | F21S 10/046 |
| 10,948,145 B2* | 3/2021 | Hurduc | | F21S 10/046 |
| 10,948,146 B2* | 3/2021 | Li | | F21V 23/0407 |
| 10,989,381 B2* | 4/2021 | Schnuckle | | F21S 6/001 |
| 2005/0169812 A1* | 8/2005 | Helf | | A01M 1/04 422/123 |
| 2007/0159422 A1* | 7/2007 | Blandino | | H05B 45/37 345/82 |
| 2007/0292812 A1* | 12/2007 | Furner | | F23D 3/24 431/289 |
| 2010/0124050 A1* | 5/2010 | Hau | | F21V 3/02 362/183 |
| 2011/0019422 A1* | 1/2011 | Schnuckle | | F21K 9/23 362/277 |
| 2011/0127914 A1* | 6/2011 | Patton | | F21V 17/10 315/76 |
| 2012/0134157 A1* | 5/2012 | Li | | F21S 10/046 362/277 |
| 2012/0300459 A1* | 11/2012 | Hau | | F21K 9/23 362/249.02 |
| 2014/0211499 A1* | 7/2014 | Fong | | F21S 6/001 362/558 |
| 2014/0241004 A1* | 8/2014 | Chen | | F21S 6/001 362/569 |
| 2015/0036348 A1* | 2/2015 | Dong | | F21V 9/08 362/293 |
| 2015/0103520 A1* | 4/2015 | Fournier | | F21S 9/02 362/190 |
| 2015/0204498 A1* | 7/2015 | Hau | | F21S 10/046 362/650 |
| 2016/0109081 A1* | 4/2016 | Thompson | | F21S 9/02 362/96 |
| 2016/0290579 A1* | 10/2016 | Au | | F21S 6/001 |
| 2017/0067608 A1* | 3/2017 | Patton | | A61L 9/122 |
| 2017/0089548 A1* | 3/2017 | Yang | | F21L 4/02 |
| 2017/0122511 A1* | 5/2017 | Ding | | F21V 17/002 |
| 2017/0122512 A1* | 5/2017 | Yuan | | F21S 10/04 |
| 2017/0159901 A1* | 6/2017 | Li | | F21S 10/046 |
| 2018/0283633 A1* | 10/2018 | Roberts | | H05B 45/20 |
| 2018/0292058 A1* | 10/2018 | Li | | A61L 9/035 |
| 2019/0041012 A1* | 2/2019 | Fang | | F21S 10/002 |
| 2019/0063703 A1* | 2/2019 | Hurduc | | F21S 10/046 |
| 2019/0195447 A1* | 6/2019 | Wu | | A61L 9/122 |
| 2019/0316747 A1* | 10/2019 | Dong | | F21S 10/046 |
| 2020/0114038 A1* | 4/2020 | Yuan | | F21S 9/02 |
| 2020/0217469 A1* | 7/2020 | Fan | | F21S 10/046 |

* cited by examiner

ELECTRONIC ARTIFICIAL CANDLE

CROSS-REFERENCE TO RELATED APPLICATIONS

This application is a Continuation Application of PCT Application No. PCT/CN2017/117593 filed on Dec. 21, 2017, the entire contents of which are hereby incorporated by reference.

TECHNICAL FIELD

The present invention relates to the field of illumination techniques, and more particularly to an electronic artificial candle.

BACKGROUND

In pursuit of a living space that is comfortable and elegant, much attention has been payed to create a desirable atmosphere for the indoor environment, and electronic artificial candles are commonly utilized to alter the indoor atmosphere.

In existing electronic artificial candles, light ray emitted by an LED is impinged on a flame sheet to emulate the flame of a conventional candle. The flame sheet is typically suspended on a hook made of a metal wire and is swung back and forth. Such a configuration is complex in installation and low in production efficiency, thereby resulting in a high cost or production. Other flame sheets may take the form of a hook. Such a configuration may involve a complex mold, a high defect rate, and tendency of the flame sheet to fall off.

In addition, some electronic artificial candles also use a fan to blow essential oils in order to fill the indoor space with fragrance. However, the resulting fragrance is neither widespread nor strong enough.

SUMMARY

It is an objective of the present invention to overcome the disadvantages of prior art mentioned above by providing an electronic artificial candle with a low cost and wide-spread fragrance.

In view of this, the present invention provides an electronic artificial candle, comprising a barrel of a hollow structure with a closed top and an opened bottom, a first through hole being formed at the top of the barrel, a mounting tube being provided inside the barrel and fixed to an inner surface of the top of the barrel, the mounting tube having a hollow structure with an opened top and an opened bottom, the barrel and the mounting tube being coaxially arranged, an elongate first bracket being snap-fitted to the top of the mounting tube, the first bracket being arranged along a radial direction of the mounting tube, the first bracket being depressed at a middle portion thereof, a second bracket being suspended at the depressed portion of the first bracket and vertically arranged and freely swingable, an upper portion of the second bracket passing through the first through hole and a lower portion of the second bracket being arranged inside the barrel, a flame cover that is hollow and transparent being fixed to the top of the second bracket, the flame cover being arranged outside the barrel, at least one LED being fixed inside the flame cover, at least one magnet being fixed to a lower end of the second bracket, a magnetic coil being fixed to the bottom of the mounting tube, the LED and the magnetic coil being electrically connected to a power control board, and the power control board being configured to supply stable direct current to the LED and intermittent direct current to the magnetic coil.

Further, the electronic artificial candle comprises a candle tube also of a hollow structure with a closed top and an opened bottom, the candle tube being arranged around an outer surface of the barrel, the candle tube and the barrel being coaxially arranged, a second through hole being formed at the top of the candle tube, the first through hole and second through hole being arranged opposite to and in communication with each other, and the upper portion of the second bracket also passing through the second through hole.

Specifically, the second bracket comprises a square frame, the first bracket passing through the inner space of the square frame, two clips being fixed to the bottom of the square frame and the two clips being directed vertically downward, spaced apart, and parallel to each other, a pendulum being fixed between the two clips, an inverted cone being fixed to the middle of the inner wall of the top of the square frame, an inverted-conical slot being formed at the middle of the first bracket, a tip of the inverted cone being abutted against a bottommost side of the inverted-conical slot, a cylinder being fixed to the middle of the outer wall of the top of the square frame, and the LED being fixed to a top of the cylinder.

Specifically, the square frame, the clip, the pendulum, the inverted cone, and the cylinder are formed integrally from plastic through injection molding.

Specifically, the flame cover has a water-drop shape, and the LED is positioned inside a lower portion of the flame cover.

Further, a snap ring is fixed inside the first through hole and is snap-fitted to the mounting tube.

Further, an aromatherapy device is provided at the bottom of the barrel, the aromatherapy device comprising a bottom plate connected fixedly to the bottom of the barrel, a first fixing tube and a second fixing tube being fixed to the bottom plate, and the first fixing tube and the second fixing tube both having a structure with an opened top and a closed bottom;

an essential-oil vial with an opened top and a closed bottom is fixed inside the first fixing tube, the essential-oil vial being filled with essential oil, a suction pipe being further vertically provided inside the essential-oil vial, an atomizer being provided at a top of the essential-oil vial, the atomizer being in communication with the essential-oil vial, a vent pipe being provided horizontally at a side wall of the atomizer, an atomizer cap being provided on the top of the atomizer, a fragrance-spray orifice being provided at the atomizer cap, a fragrance-spray pipe being connected to the fragrance-spray orifice, and the fragrance-spray pipe extending to the first through hole of the barrel; and an airflow generator is fixed inside the second fixing tube, the airflow generator being electrically connected to the power control board, an outlet pipe being provided at the top of the airflow generator, the outlet pipe being connected to a cylindrical nozzle, and the nozzle passing through the vent pipe in the side wall of the atomizer and extending to an opening at an upper end of the suction pipe.

Further, an end cap is fixed to the opening at the top of the second fixing tube.

Further, a support post is fixed to an upper surface of the end cap, the top of the support post being fixedly connected to the bottom of the mounting tube.

According to the present invention, an elongate first bracket is snap-fitted to the top of the mounting tube. The first bracket is connected to the mounting tube in a convenient and secure manner, so that the first bracket will not fall off the mounting tube, thereby enabling long-time and stable swinging of the second bracket on the first bracket. In contrast to prior art, the first bracket and the mounting tube of the present invention can be fabricated separately in mass production. The first bracket and the mounting tube can be fabricated from a mold of a simple structure, thereby reducing the cost of production and the defect rate and improving the production efficiency.

BRIEF DESCRIPTION OF THE DRAWINGS

In order to explain the technical solutions of the present invention more clearly, the drawings that need to be used in the embodiments will be briefly described below. Obviously, the drawings in the following description show merely some embodiments of the present invention. Other drawings can be obtained on the basis of these drawings without any creative effort by those of ordinary skill in the art.

DESCRIPTION OF THE EMBODIMENTS

Figure 1:
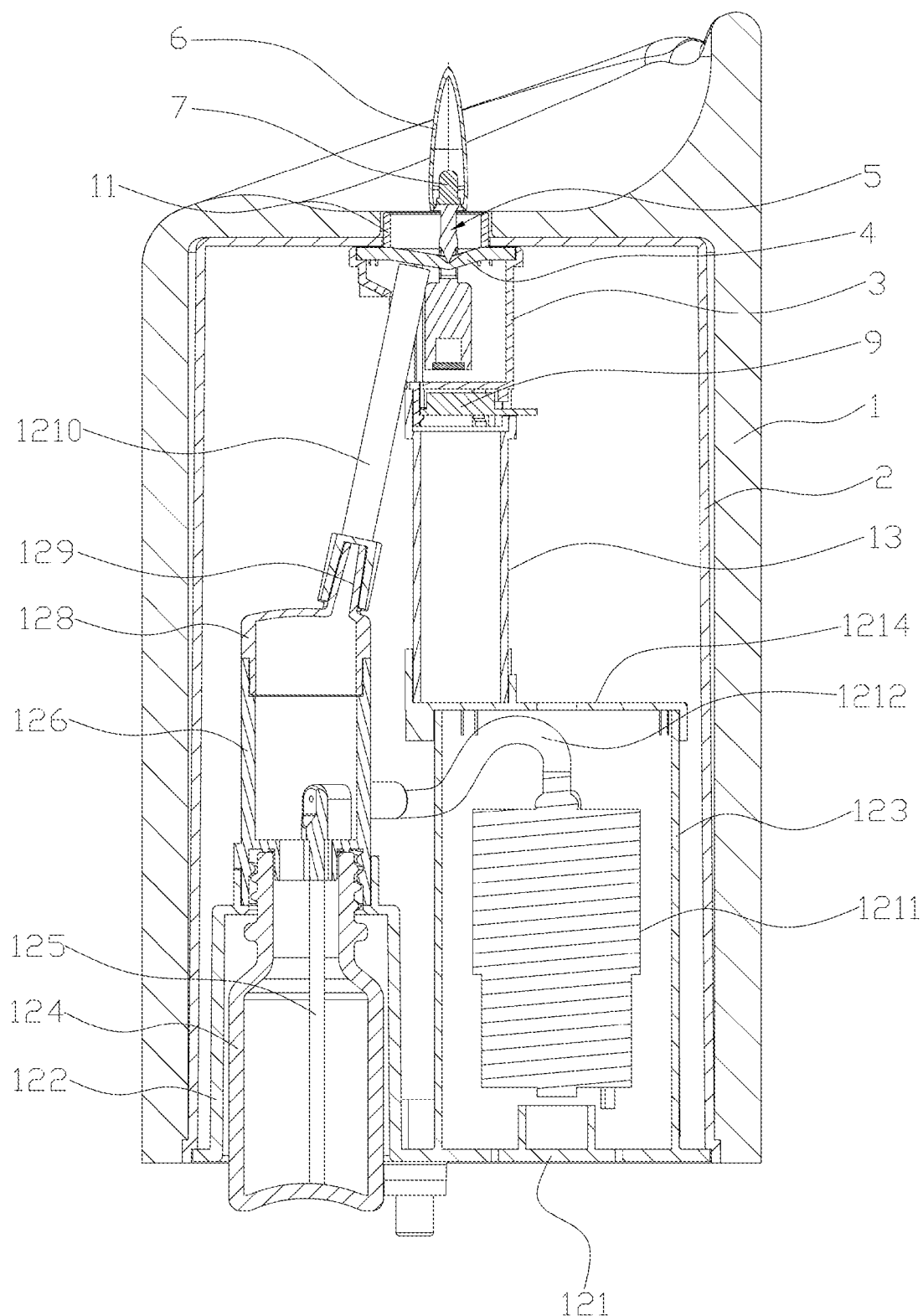
FIG. 1 is a schematic view showing an internal structure of an electronic artificial candle according to an embodiment of the present invention.

The technical solutions in the embodiments of the present invention will be described clearly and thoroughly with reference to the drawings in the embodiments of the present invention.

As shown in FIGS. 1 to 4, an electronic artificial candle according to an embodiment of the present invention comprises a candle tube 1 and a barrel 2, both of a hollow structure with a closed top and an opened bottom. The candle tube 1 is arranged around an outer surface of the barrel 2. A first through hole 21 is formed at the top of the barrel 2, and a second through hole 11 is formed at the top of the candle tube 1. The first through hole 21 and the second through hole 11 are arranged opposite to and in communication with each other. A mounting tube 3 is fixed inside the barrel 2 on the inner surface of the top of the barrel 2. The mounting tube 3 has a hollow structure with an opened top and bottom. The candle tube 1, the barrel 2, and the mounting tube 3 are all coaxially arranged. An elongate first bracket 4 is snap-fitted to the top of the mounting tube 3, i.e., the mounting tube 3 and the first bracket 4 are snap-fitted to each other. The first bracket 4 is arranged along a radially direction of the mounting tube 3. The first bracket 4 is depressed at the middle. A second bracket 5 is suspended at the depression of the first bracket 4 and is vertically arranged and freely swingable. An upper portion of the second bracket 5 passes through the first through hole 21 and the second through hole 11, and a lower portion of the second bracket 5 is arranged inside the barrel 2. A flame cover 6 that is hollow and transparent is fixed to the top of the second bracket 5. The flame cover 6 is provided outside the candle tube 1 and the barrel 2. At least one LED 7 is fixed inside the flame cover 6. At least one magnet 8 is fixed to a lower end of the second bracket 5. A magnetic coil 9 is fixed to the bottom of the mounting tube 3. The LED 7 and the magnetic coil 9 are electrically connected to a power control board 10 respectively. The power control board 10 is configured to supply stable direct current to the LED 7 and supply intermittent direct current to the magnetic coil 9.

The electronic artificial candle according to the present invention is operated as follows. The power control board 10 supplies stable direct current to the LED 7 to place the LED 7 in an always-on status. When the power control board 10 supplies direct current to the magnetic coil 9, the magnetic coil 9 is energized and generates a magnetic field. The magnetic force from the magnetic field repels the magnet 8 to cause the magnet 8 to move away from the magnetic coil 9. When no direct current is supplied to the magnetic coil 9 from the power control board 10, the magnetic field generated by the magnetic coil 9 disappears. Thus, the magnet 8 moves toward the magnetic coil 9 under its own weight, thereby resulting in swinging back and forth of the magnet 8. The second bracket 5 and the flame cover 6 swing back and forth along with the magnet 8. The swinging back and forth of the flame cover 6 emulates wavering of the flame during burning of a candle.

According to the present invention, an elongate first bracket 4 is snap-fitted to the top of the mounting tube 3. The first bracket 4 is connected to the mounting tube 3 in a convenient and secure manner, so that the first bracket 4 will not fall off the mounting tube 3, thereby enabling long-time and stable swinging of the second bracket 5 on the first bracket 4. In contrast to prior art, the first bracket 4 and the mounting tube 3 of the present invention can be fabricated separately in mass production. The first bracket 4 and the mounting tube 3 can be fabricated from a mold of a simple structure, thereby reducing the cost of production and the defect rate and improving the production efficiency.

A detailed description will be made below of various components of the electronic artificial candle according to the present invention.

Specifically, the candle tube 1 is made of paraffin wax, the barrel 2, mounting tube 3, first bracket 4, and second bracket 5 are all made of plastic, such as PP, ABS, or PMMA, and the flame cover 51 is made of transparent plastic, such as PP, ABS, or PMMA.

Figure 4:
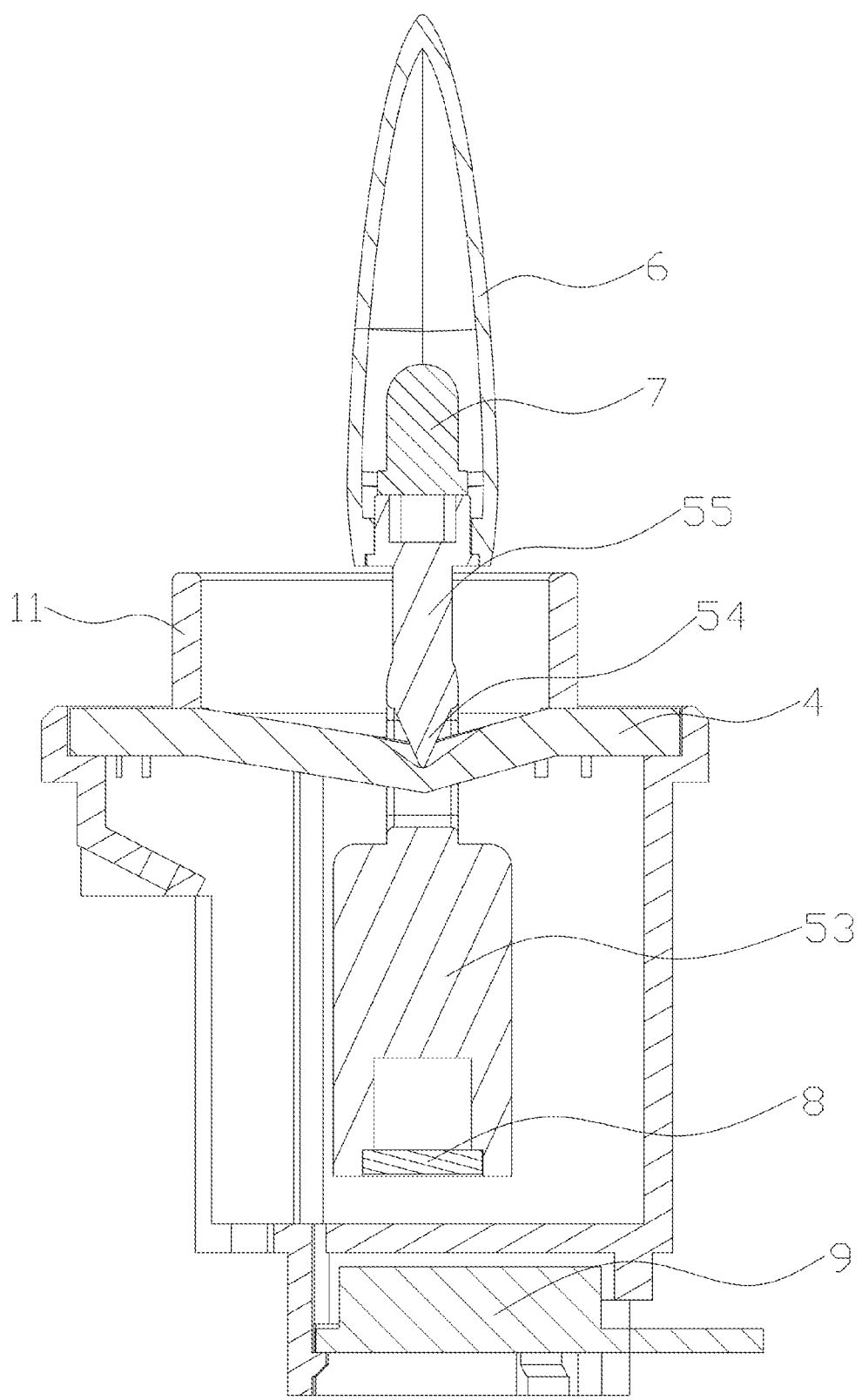
FIG. 4 is a schematic view showing assembly of a second bracket, a flame cover, and a magnetic coil in an electronic artificial candle according to an embodiment of the present invention.
Figure 5:
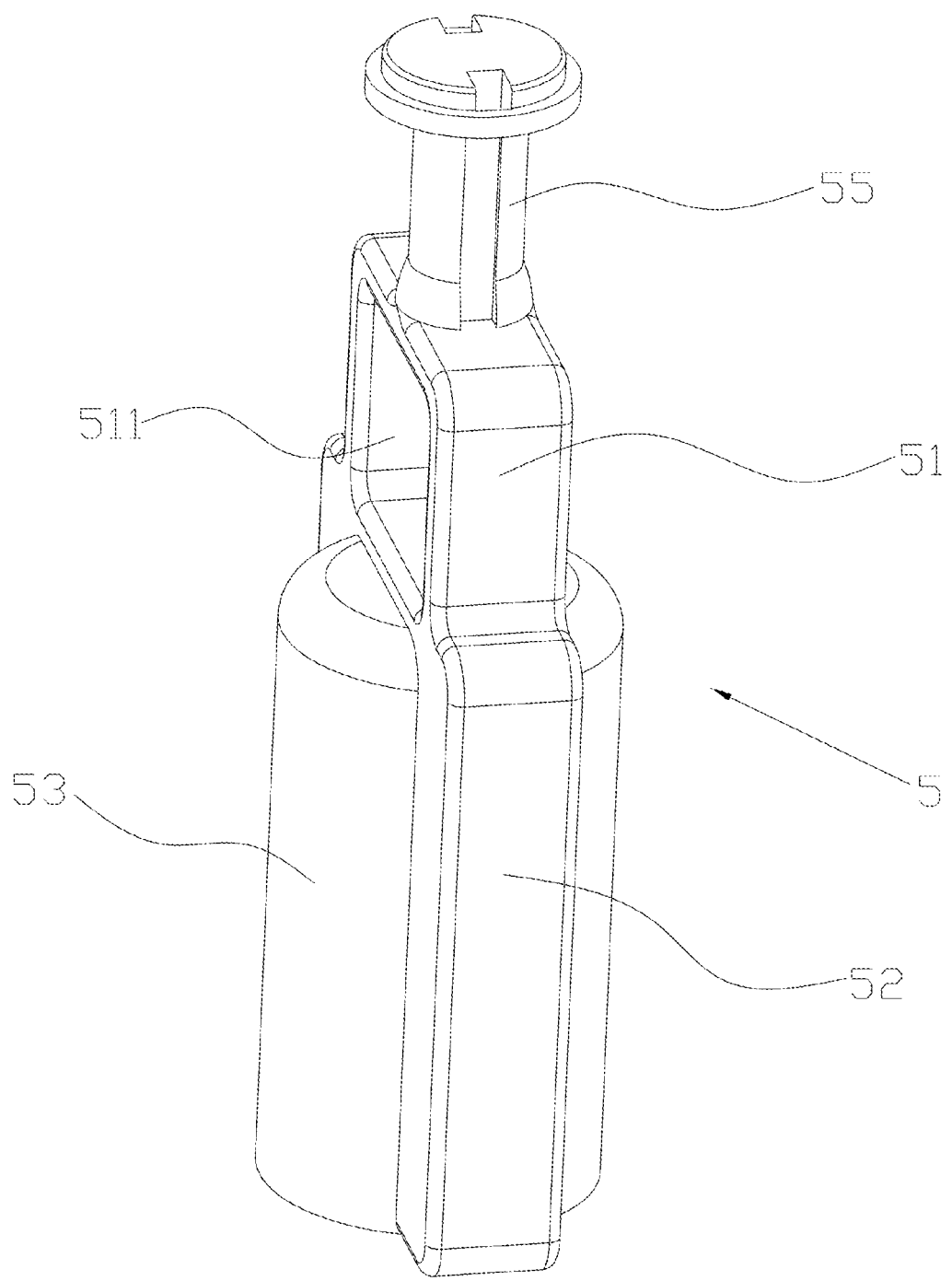
FIG. 5 is a schematic view showing assembly of a second bracket in an electronic artificial candle according to an embodiment of the present invention.

As shown in FIGS. 4 and 5, specifically, the second bracket 5 is suspended on the first bracket 4 specifically in the following manner. The second bracket 5 comprises a square frame 51. The first bracket 4 passes through an inner space 511 of the square frame 51. Two clips 52 are fixed to the bottom of the square frame 51 and directed vertically downward, spaced apart, and parallel to each other. A pendulum 53 is fixed between the two clips 52. An inverted cone 54 is fixed to the middle of the inner wall of the top of the square frame 51. An inverted-conical slot 41 is formed at the middle of the first bracket 4. The tip of the inverted cone 54 is abutted against a bottommost portion of the inverted-conical slot 41, thereby allowing the second bracket 5 to be suspended on the first bracket 4 and capable of swinging freely on the first bracket 4. A cylinder 55 is fixed to the middle of the outer wall of the top of the square frame 51. The LED 7 is fixed to the top of the cylinder 55. As the tip of the inverted cone 54 at the middle of the inner wall of the top of the square frame 51 is abutted against the inverted-conical slot 41 formed at the middle of the first bracket 4, the inverted cone 54 can swing freely within the inverted-conical slot 41 without falling off the inverted-conical slot 41. As such, it is ensured that the inverted cone 54 can swing stably within the inverted-conical slot 41 for a long time, and consequently that the second bracket 5 can swing freely and stably on the first bracket 4 along with the flame cover 6 for a long time, thereby resulting in more vivid emulation of a wavering flame of a burning candle.

Specifically, the square frame 51, the clips 52, the pendulum 53, the inverted cone 54, and the cylinder 55 are formed integrally from plastic, such as PP, ABS, PMMA, or the like, through injection molding.

Specifically, the flame cover 6 has a water-drop shape. The LED 7 is positioned inside a lower portion of the flame cover 6. The water-drop-shaped flame cover 6 may refract light emitted by the LED 7, allowing more wide-spread illumination by the LED 7.

Specifically, the LED 7 flickers under control of an IC, so that the emulated flame appears more like the flame of a burning candle and exhibits more vivid wavering. The LED 7 is dimmed gradually and then lighted up gradually under control of a microprocessor, thereby further improving emulation of a burning flame. Meanwhile, the microprocessor controls the on and off time of the LED 7 by controlling turning on and off of the LED 7 through a built-in program. The light ray at the LED 7 is the brightest. A bright light core extending outward from the LED 7 is created within the flame cover 6. As the light becomes gradually weaker, a relatively dark light ring is created within the flame cover 6. In this way, a sense of layering is created.

As shown in FIGS. 1 and 4, specifically, the mounting tube 3 is fixed to the inner surface of the top of the barrel 2 in the following manner. A snap ring 11 is fixed within the first through hole 21 in the barrel 2 through interference fitting. The snap ring 11 is snap-fitted to the mounting tube 3, so as to fix the mounting tube 3 to the inner surface of the top of the barrel 2.

Figure 2:
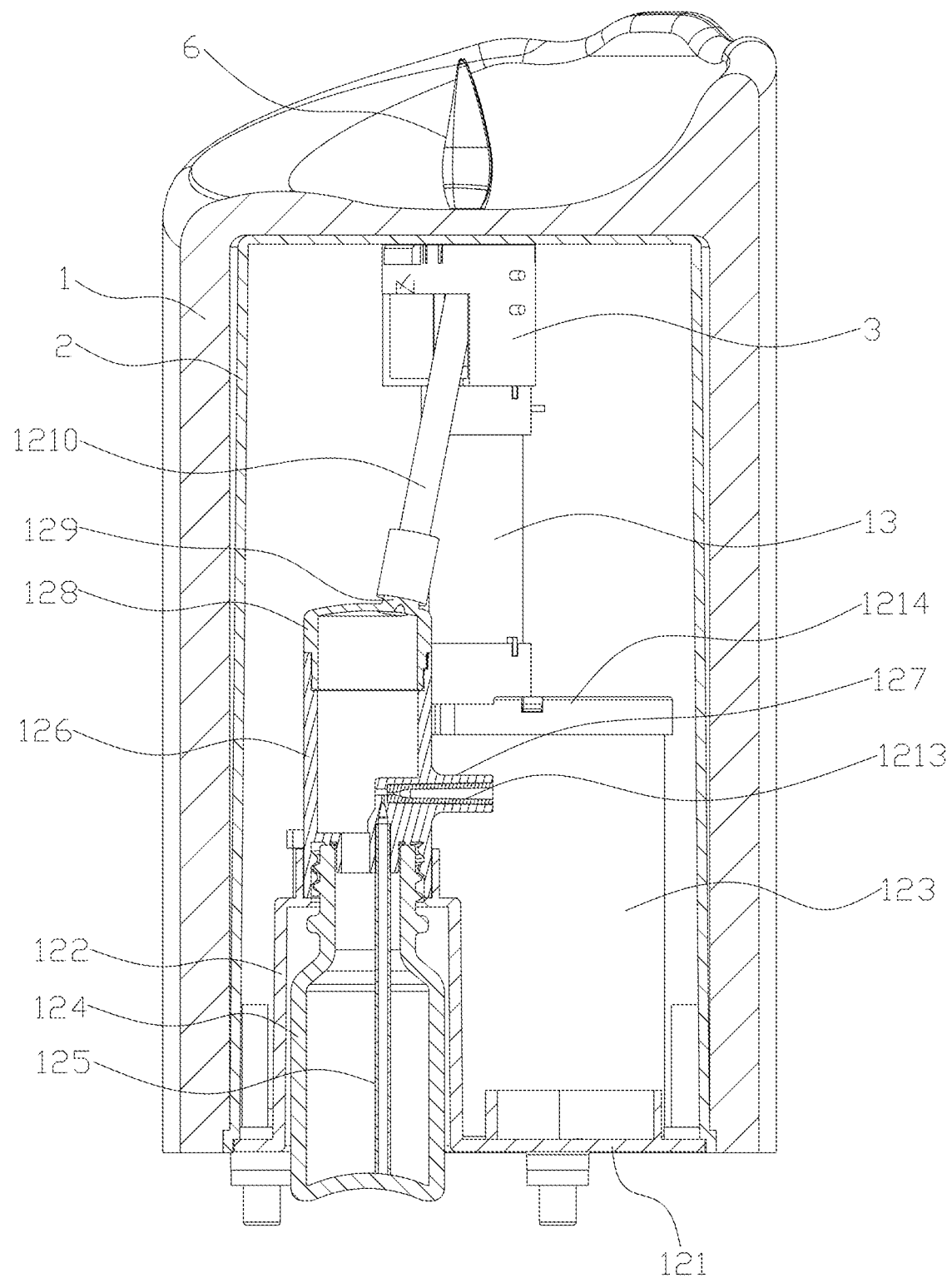
FIG. 2 is another schematic view showing an internal structure of an electronic artificial candle according to an embodiment of the present invention.
Figure 3:
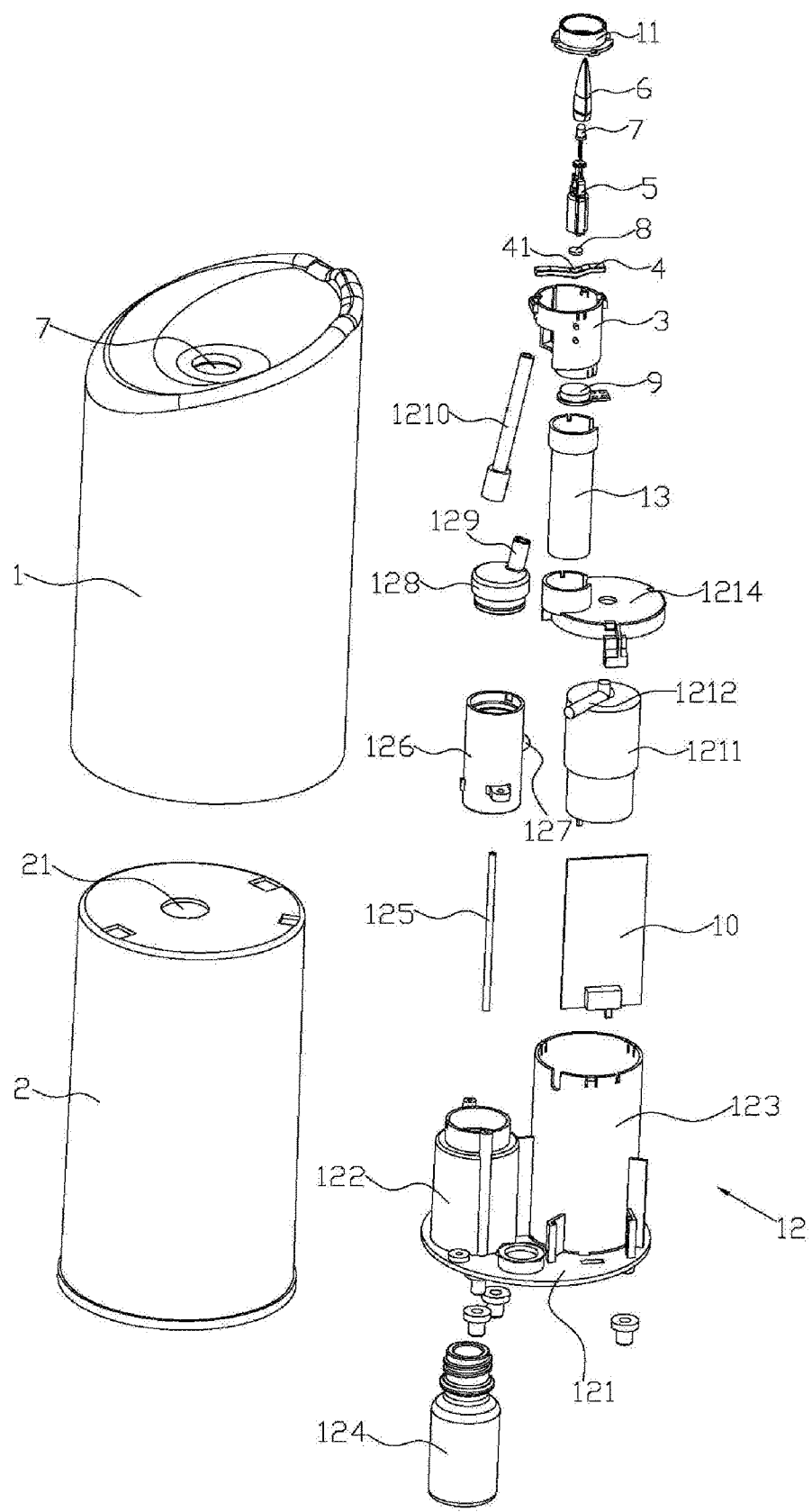
FIG. 3 is an exploded schematic view of an electronic artificial candle according to an embodiment of the present invention.

As shown in FIGS. 1 to 3, an aromatherapy device 12 is further provided at the bottom of the barrel 2. The aromatherapy device 12 comprises a bottom plate 121 connected fixedly to the bottom of the barrel 2. A first fixing tube 122 and a second fixing tube 123 are fixed to the bottom plate 121. The first fixing tube 122 and the second fixing tube 123 both have a structure with an opened top and a closed bottom.

An essential-oil vial 124 with an opened top and a closed bottom is fixed inside the first fixing tube 122. The essential-oil vial 124 is filled with essential oil. A suction pipe 125 is further provided vertically inside the essential-oil vial 124. An atomizer 126 is provided on the top of the essential-oil vial 124. The atomizer 126 is in communication with the essential-oil vial 124. A vent pipe 127 is provided horizontally at a side wall of the atomizer 126. An atomizer cap 128 is provided on the top of the atomizer 126. A fragrance-spray orifice 129 is provided on the atomizer cap 128. A fragrance-spray pipe 1210 is connected to the fragrance-spray orifice 129, and the fragrance-spray pipe 1210 extends to the first through hole 21 of the barrel 2.

An airflow generator 1211 is fixed inside the second fixing tube 123. The airflow generator 1211 is electrically connected to the power control board 10. An outlet pipe 1212 is provided at the top of the airflow generator 1211. The outlet pipe 1212 is connected to a cylindrical nozzle 1213. The nozzle 1213 passes through the vent pipe 127 in the side wall of the atomizer 126 and extends to an opening at the upper end of the suction pipe 125. An end cap 1214 is provided at the opening at the top of the second fixing tube 123.

The aromatherapy device 12 of the present invention is operated as follows. The power control board 10 supplies power to the airflow generator 1211. Once started, the airflow generator 1211 generates a high-speed airflow. The high-speed airflow passes through the nozzle 1213 into the opening of the upper end of the suction pipe 125 inside the atomizer 126. The high-speed airflow causes the air pressure at the opening of the upper end of the suction pipe 125 to drop, so that a pressure difference is created between this air pressure and the air pressure inside the essential-oil vial 124 (i.e., the air pressure at the opening of the upper end of the suction pipe 125 is less than that inside the essential-oil vial 124). Due to the difference between these air pressures, the essential oil in the essential-oil vial 124 flows to the opening of the upper end of the suction pipe 125 along the suction pipe 125. Then the high-speed airflow blows the essential oil at the opening of the upper end of the suction pipe 125 into an oil spray which impacts on the inner wall of the atomizer 126 along with the high-speed airflow to produce anion oil particles. Since the anion oil particles produced have a density less than the density of air inside the atomizer 126, the anion oil particles will be dispersed out of the electronic artificial candle sequentially along the fragrance-spray orifice 129, the fragrance-spray pipe 1210, and the first through hole 21, so that the fragrance of the essential oil is blended into the air inside the room and spread to various regions with flow of the air inside the room.

In the present invention, the essential oil is dispersed throughout the room through cold spray by using impact of the high-speed airflow, obviating the need for adding water, heating, or combustion. Therefore, the composition of the essential oil is not destroyed, and thus the original organic activity of the essential oil can be preserved. Meanwhile, the molecules of the essential oil can be dispersed throughout the air inside the room, providing wide-spread fragrance and producing numerous anion oil particles. Through reaction with harmful gas molecules in the air, these anion oil particles can eliminate harmful substances, such as formaldehyde, benzene, ammonia, TVOC, etc., for the purposes of air purification, stress relief, healthcare, and improved sleep quality.

Further, a support post 13 is fixed to the upper surface of the end cap 1214. The top of the support post 13 is fixedly connected to the bottom of the mounting tube 3 through snap-fitting. The support post 13 serves to support and fix the mounting tube 3.

Describe above are preferred embodiments of the present invention, and it should be noted that numerous modifications and alternations can be made by those of ordinary skill in the art without departing from the spirit of the present invention, and these modifications and alternations shall fall within the scope of the present invention.

What is claimed is:

1. An electronic artificial candle, comprising a barrel of a hollow structure with a closed top and an opened bottom, a first through hole being formed at the top of the barrel, wherein a mounting tube is provided inside the barrel and fixed to an inner surface of the top of the barrel, the mounting tube has a hollow structure with an opened top and an opened bottom, the barrel and the mounting tube are coaxially arranged, an elongate first bracket is snap-fitted to the top of the mounting tube, the first bracket is arranged along a radial direction of the mounting tube, the first bracket is depressed at a middle portion thereof, a second bracket is suspended at a depressed portion of the first bracket and vertically arranged and freely swingable, an upper portion of the second bracket passes through the first through hole and a lower portion of the second bracket is arranged inside the barrel, a flame cover that is hollow and transparent is fixed to the top of the second bracket, the flame cover is arranged outside the barrel, at least one LED is fixed inside the flame cover, at least one magnet is fixed to a lower end of the second bracket, a magnetic coil is fixed to the bottom of the mounting tube, the LED and the magnetic coil are electrically connected to a power control board, and the power control board is configured to supply stable direct current to the LED and intermittent direct current to the magnetic coil;

wherein the second bracket comprises a square frame, the first bracket passing through an inner space of the square frame, two clips being fixed to the bottom of the square frame and the two clips being directed vertically downward, spaced apart, and parallel to each other, a pendulum being fixed between the two clips, an inverted cone being fixed to a middle portion of the inner wall of the top of the square frame, an inverted-conical slot being formed at the middle portion of the first bracket, a tip of the inverted cone being abutted against a bottommost side of the inverted-conical slot, a cylinder being fixed to a middle portion of the outer wall of the top of the square frame, and the LED being fixed to the top of the cylinder.

2. The electronic artificial candle of claim 1, wherein the electronic artificial candle further comprises a candle tube of a hollow structure with a closed top and an opened bottom, the candle tube being arranged around an outer surface of the barrel, the candle tube and the barrel being coaxially arranged, a second through hole being formed at the top of the candle tube, the first through hole and second through hole being arranged opposite to and in communication with each other, and the upper portion of the second bracket passing through the second through hole.

3. The electronic artificial candle of claim 1, wherein the square frame, the clips, the pendulum, the inverted cone, and the cylinder are formed integrally from plastic through injection molding.

4. The electronic artificial candle of claim 1, wherein the flame cover has a water-drop shape, and the LED is positioned inside a lower portion of the flame cover.

5. The electronic artificial candle of claim 1, wherein a snap ring is fixed inside the first through hole and is snap-fitted to the mounting tube.

6. The electronic artificial candle of claim 1, wherein an aromatherapy device is provided at the bottom of the barrel, and the aromatherapy device comprises a bottom plate connected fixedly to the bottom of the barrel, a first fixing tube and a second fixing tube fixed to the bottom plate, and wherein the first fixing tube and the second fixing tube both have a structure with an opened top and a closed bottom;

wherein an essential-oil vial with an opened top and a closed bottom is fixed inside the first fixing tube, the essential-oil vial is filled with an essential oil, a suction pipe is further vertically provided inside the essential-oil vial, an atomizer is provided at the top of the essential-oil vial, the atomizer is in communication with the essential-oil vial, a vent pipe is provided horizontally at a side wall of the atomizer, an atomizer cap is provided on a top of the atomizer, a fragrance-spray orifice is provided at the atomizer cap, a fragrance-spray pipe is connected to the fragrance-spray orifice, and the fragrance-spray pipe extends to the first through hole of the barrel; and wherein an airflow generator is fixed inside the second fixing tube, the airflow generator is electrically connected to the power control board, an outlet pipe is provided at the top of the airflow generator, the outlet pipe is connected to a cylindrical nozzle, and the nozzle passes through the vent pipe at the side wall of the atomizer and extends to an opening at the upper end of the suction pipe.

7. The electronic artificial candle of claim 6, wherein an end cap is fixed to an opening at the top of the second fixing tube.

8. The electronic artificial candle of claim 6, wherein a support post is fixed to an upper surface of the end cap, and the top of the support post is fixedly connected to the bottom of the mounting tube.

9. An electronic artificial candle, comprising a barrel of a hollow structure with a closed top and an opened bottom, a first through hole being formed at the top of the barrel, wherein a mounting tube is provided inside the barrel and fixed to an inner surface of the top of the barrel, the mounting tube has a hollow structure with an opened top and an opened bottom, the barrel and the mounting tube are coaxially arranged, an elongate first bracket is snap-fitted to the top of the mounting tube, the first bracket is arranged along a radial direction of the mounting tube, the first bracket is depressed at a middle portion thereof, a second bracket is suspended at a depressed portion of the first bracket and vertically arranged and freely swingable, an upper portion of the second bracket passes through the first through hole and a lower portion of the second bracket is arranged inside the barrel, a flame cover that is hollow and transparent is fixed to the top of the second bracket, the flame cover is arranged outside the barrel, at least one LED is fixed inside the flame cover, at least one magnet is fixed to a lower end of the second bracket, a magnetic coil is fixed to the bottom of the mounting tube, the LED and the magnetic coil are electrically connected to a power control board, and the power control board is configured to supply stable direct current to the LED and intermittent direct current to the magnetic coil;

wherein an aromatherapy device is provided at the bottom of the barrel, and the aromatherapy device comprises a bottom plate connected fixedly to the bottom of the barrel, a first fixing tube and a second fixing tube fixed to the bottom plate, and wherein the first fixing tube and the second fixing tube both have a structure with an opened top and a closed bottom;

wherein an essential-oil vial with an opened top and a closed bottom is fixed inside the first fixing tube, the essential-oil vial is filled with an essential oil, a suction pipe is further vertically provided inside the essential-oil vial, an atomizer is provided at the top of the essential-oil vial, the atomizer is in communication with the essential-oil vial, a vent pipe is provided horizontally at a side wall of the atomizer, an atomizer cap is provided on a top of the atomizer, a fragrance-spray orifice is provided at the atomizer cap, a fragrance-spray pipe is connected to the fragrance-spray orifice, and the fragrance-spray pipe extends to the first through hole of the barrel; and wherein an airflow generator is fixed inside the second fixing tube, the airflow generator is electrically connected to the power control board, an outlet pipe is provided at the top of the airflow generator, the outlet pipe is connected to a cylindrical nozzle, and the nozzle passes through the vent pipe at the side wall of the atomizer and extends to an opening at the upper end of the suction pipe.

10. The electronic artificial candle of claim 9, wherein the electronic artificial candle further comprises a candle tube of a hollow structure with a closed top and an opened bottom, the candle tube being arranged around an outer surface of the barrel, the candle tube and the barrel being coaxially arranged, a second through hole being formed at the top of the candle tube, the first through hole and second through hole being arranged opposite to and in communication with each other, and the upper portion of the second bracket passing through the second through hole.

11. The electronic artificial candle of claim 9, wherein the flame cover has a water-drop shape, and the LED is positioned inside a lower portion of the flame cover.

12. The electronic artificial candle of claim 9, wherein a snap ring is fixed inside the first through hole and is snap-fitted to the mounting tube.

13. The electronic artificial candle of claim 9, wherein an end cap is fixed to an opening at the top of the second fixing tube.

14. The electronic artificial candle of claim 9, wherein a support post is fixed to an upper surface of the end cap, and the top of the support post is fixedly connected to the bottom of the mounting tube.

\* \* \* \* \*